(12) United States Patent
Mikuszeit

(10) Patent No.: US 12,257,005 B2
(45) Date of Patent: *Mar. 25, 2025

(54) TRACKING A SENSOR THAT INCLUDES A FERROFLUID

(71) Applicant: Northern Digital Inc., Waterloo (CA)

(72) Inventor: Nikolai Mikuszeit, Radolfzell (DE)

(73) Assignee: Northern Digital Inc., Waterloo (CA)

( * ) Notice: Subject to any disclaimer, the term of this patent is extended or adjusted under 35 U.S.C. 154(b) by 0 days.

This patent is subject to a terminal disclaimer.

(21) Appl. No.: 17/951,284

(22) Filed: Sep. 23, 2022

(65) Prior Publication Data

US 2023/0018001 A1    Jan. 19, 2023

Related U.S. Application Data

(63) Continuation of application No. 16/047,122, filed on Jul. 27, 2018, now Pat. No. 11,529,193.

(60) Provisional application No. 62/543,686, filed on Aug. 10, 2017.

(51) Int. Cl.
| | |
|---|---|
| *A61B 34/20* | (2016.01) |
| *A61B 5/06* | (2006.01) |
| *A61B 90/00* | (2016.01) |
| *A61K 49/00* | (2006.01) |
| *G01D 5/20* | (2006.01) |

(52) U.S. Cl.
CPC .............. *A61B 34/20* (2016.02); *A61B 5/062* (2013.01); *A61B 90/39* (2016.02); *A61K 49/0002* (2013.01); *G01D 5/2013* (2013.01); *A61B 2034/2051* (2016.02); *A61B 2034/2072* (2016.02); *A61B 2090/3933* (2016.02); *A61B 2090/3954* (2016.02); *A61B 2090/3958* (2016.02)

(58) Field of Classification Search
CPC ...................................................... A61B 34/20
See application file for complete search history.

(56) References Cited

U.S. PATENT DOCUMENTS

| | | |
|---|---|---|
| 2,753,469 A | 7/1956 | Statham et al. |
| 3,306,113 A | 2/1967 | Tuccinardi |
| 3,516,294 A | 6/1970 | Schmieder |

(Continued)

FOREIGN PATENT DOCUMENTS

| | | |
|---|---|---|
| CN | 101103919 | 1/2008 |
| CN | 101120877 | 2/2008 |

(Continued)

*Primary Examiner* — Hyun D Park
(74) *Attorney, Agent, or Firm* — Fish & Richardson P.C.

(57) ABSTRACT

A system comprising: one or more field generating coils configured to generate a magnetic field; a sensor comprising a shell that contains a ferrofluid, the sensor configured to be introduced in proximity to the magnetic field, wherein the ferrofluid causes distortion of the magnetic field when the ferrofluid is in proximity to the magnetic field; and one or more field measuring coils configured to: measure a characteristic of the magnetic field when the ferrofluid is in proximity to the magnetic field; and provide, to a computing device, a signal representative of the measured characteristic of the magnetic field, wherein the computing device is configured to determine one or both of a position and an orientation of the sensor based on the measured characteristic of the magnetic field.

19 Claims, 5 Drawing Sheets

(56) References Cited

U.S. PATENT DOCUMENTS

| | | |
|---|---|---|
| 4,023,278 A | 5/1977 | Hoyt |
| 4,047,439 A | 9/1977 | Russell et al. |
| 4,557,667 A | 12/1985 | Delassus et al. |
| 4,718,276 A | 1/1988 | Laughlin |
| 4,808,079 A | 2/1989 | Crowley et al. |
| 4,818,185 A | 4/1989 | Alexeff |
| 4,905,517 A | 3/1990 | Crowe et al. |
| 4,922,753 A | 5/1990 | Idogaki et al. |
| 4,984,463 A | 1/1991 | Idogaki et al. |
| 4,991,438 A | 2/1991 | Evans |
| 5,007,292 A | 4/1991 | Crowe et al. |
| 5,461,919 A | 10/1995 | Laughlin |
| 5,665,912 A | 9/1997 | Laughlin |
| 5,780,741 A | 7/1998 | Raj |
| 5,908,987 A | 6/1999 | Raj |
| 6,173,611 B1 | 1/2001 | Laughlin |
| 6,374,673 B1 | 4/2002 | Schendel |
| 7,074,175 B2 | 7/2006 | Handy et al. |
| 7,175,912 B2 | 2/2007 | Cui et al. |
| 7,178,399 B2 | 2/2007 | Simonenko et al. |
| 7,204,581 B2 | 4/2007 | Peeters |
| 7,296,469 B2 | 11/2007 | Simonenko et al. |
| 7,700,193 B2 | 4/2010 | Chen et al. |
| 7,819,795 B1 * | 10/2010 | Seeney ............... H04R 25/606 600/25 |
| 8,056,246 B1 | 11/2011 | Hopper et al. |
| 8,906,019 B2 | 12/2014 | Mueller |
| 8,944,067 B2 | 2/2015 | Robinson et al. |
| 9,017,713 B2 | 4/2015 | Tishin et al. |
| 9,186,317 B2 | 11/2015 | Smyth et al. |
| 9,196,405 B2 | 11/2015 | Schlenoff et al. |
| 10,779,892 B2 | 9/2020 | Mikuszeit et al. |
| 11,529,193 B2 | 12/2022 | Mikuszeit |
| 2005/0119725 A1 | 6/2005 | Wang et al. |
| 2005/0148863 A1 | 7/2005 | Okamura et al. |
| 2006/0282168 A1 * | 12/2006 | Sherman ............ A61B 17/1725 606/76 |
| 2007/0264199 A1 | 11/2007 | Labhasetwar et al. |
| 2010/0072994 A1 * | 3/2010 | Lee ..................... G01R 33/383 324/307 |
| 2010/0145337 A1 | 6/2010 | Janna |
| 2010/0274256 A1 | 10/2010 | Ritchey |
| 2011/0054237 A1 * | 3/2011 | Shapiro ................ A61P 9/00 424/9.1 |
| 2011/0144479 A1 * | 6/2011 | Hastings ............ A61B 5/6861 600/424 |
| 2012/0226094 A1 | 9/2012 | Ritchey |
| 2013/0150707 A1 | 6/2013 | Cima |
| 2014/0052020 A1 | 2/2014 | Allen |
| 2014/0081121 A1 | 3/2014 | Wilhelm |
| 2015/0294775 A1 * | 10/2015 | Rowe ..................... H02K 1/02 427/127 |
| 2016/0113683 A1 | 4/2016 | Chen et al. |
| 2018/0353304 A1 | 12/2018 | Govari |
| 2019/0046273 A1 | 2/2019 | Mikuszeit et al. |
| 2019/0046274 A1 | 2/2019 | Mikuszeit |

FOREIGN PATENT DOCUMENTS

| | | |
|---|---|---|
| CN | 102014771 | 4/2011 |
| CN | 102348477 | 2/2012 |
| CN | 102753091 | 10/2012 |
| CN | 102892364 | 1/2013 |
| CN | 105451651 | 3/2016 |

\* cited by examiner

TRACKING A SENSOR THAT INCLUDES A FERROFLUID

CROSS-REFERENCE TO RELATED APPLICATIONS

This application is a continuation application of and claims the benefit of priority under 35 U.S.C. § 120 to U.S. application Ser. No. 16/047,122, filed on Jul. 27, 2018, which claims priority to U.S. patent application Ser. No. 62/543,686, filed on Aug. 10, 2017, the entire contents of which are hereby incorporated by reference.

TECHNICAL FIELD

This disclosure relates to tracking a sensor that includes a ferrofluid.

BACKGROUND

Electromagnetic Tracking (EMT) systems are used to aid location of instruments and anatomy in medical procedures, virtual reality (VR) settings, and augmented reality (AR) settings, among others. Such systems can determine a position of a sensor based on measured distortion of a transmitted magnetic field.

SUMMARY

An Electromagnetic Tracking (EMT) system can be used to track a medical device during a medical procedure. For example, in a surgical setting, the EMT system can be used to track the position and/or orientation of a sensor incorporated in the medical device. The sensor may include a shell filled with a ferrofluid core. Magnetic properties of the sensor are configured to cause distortion in a generated magnetic field, and a field measuring coil is configured to measure characteristics of the distortion and provide such measurements to a computing device. A computing device can then determine the position and/or orientation of the sensor (and, e.g., the position and/or orientation of the medical device) based on the received measurements.

In some implementations, the sensor can be inserted into a patient's body at locations that are difficult and/or dangerous to access. For example, a flexible shell of the sensor may be inserted into the body before the ferrofluid is present. The flexible shell may allow for insertion with little or no damage to the patient's anatomy. The ferrofluid may then be provided thereafter (e.g., by being injected into the shell). Once the medical procedure has concluded, some or all of the sensor may be removed from the body. For example, the ferrofluid may be removed by piercing the shell and magnetically pulling the ferrofluid out of the body using a permanent magnet. The shell may then be removed. Alternatively, the shell may be made of a biocompatible and/or biodegradable material, and as such, may be left in the patient's body.

In one aspect, a system includes one or more field generating coils configured to generate a magnetic field. The system also includes a sensor including a shell that contains a ferrofluid. The sensor is configured to be introduced in proximity to the magnetic field. The ferrofluid causes distortion of the magnetic field when the ferrofluid is in proximity to the magnetic field. The system also includes one or more field measuring coils configured to measure a characteristic of the magnetic field when the ferrofluid is in proximity to the magnetic field. The one or more field measuring coils are also configured to provide, to a computing device, a signal representative of the measured characteristic of the magnetic field. The computing device is configured to determine one or both of a position and an orientation of the sensor based on the measured characteristic of the magnetic field.

Implementations can include one or more of the following features.

In some implementations, the one or more field measuring coils are configured to measure a characteristic of the magnetic field when the ferrofluid is not in proximity to the magnetic field. The one or more field measuring coils are also configured to provide, to the computing device, a signal representative of the measured characteristic of the magnetic field.

In some implementations, determining one or both of the position and the orientation of the sensor includes comparing the characteristic of the magnetic field measured when the ferrofluid is not in proximity to the magnetic field and the characteristic of the magnetic field measured when the ferrofluid is in proximity to the magnetic field.

In some implementations, the sensor is flexible.

In some implementations, one or more magnetic properties of the sensor remain unchanged when mechanical stress is applied to the sensor.

In some implementations, one or both of the shell and the ferrofluid are one or both of biocompatible and biodegradable.

In some implementations, the ferrofluid includes one or both of a liquid and a powder.

In some implementations, the ferrofluid includes superparamagnetic iron oxide nanoparticles (SPIONs).

In some implementations, the SPIONs include one or both of magnetite ($Fe_3O_4$) and maghemite ($\gamma$-$Fe_2O_3$).

In some implementations, the shell includes a polymer.

In some implementations, the shell is configured to be introduced into a patient's body.

In some implementations, the shell is configured to receive the ferrofluid by injection after being introduced into the patient's body.

In some implementations, the ferrofluid is configured to be removed from the shell by piercing the shell and introducing a magnetic force in proximity to the shell.

In some implementations, the sensor has an ellipsoid shape.

In some implementations, the ellipsoid is defined by three axes of unequal length.

In some implementations, the sensor has a cuboid shape.

In some implementations, the sensor has a cylindrical shape.

In some implementations, the sensor has a pill shape.

In some implementations, the sensor is wireless.

In another aspect, a wireless sensor is configured for use in an electromagnetic tracking system. The sensor includes a shell that contains a ferrofluid. The sensor is configured to be introduced in proximity to a generated magnetic field and cause distortion of the generated magnetic field. Characteristics of the distortion are representative of one or both of a position and an orientation of the sensor.

In another aspect, a method includes causing a magnetic field to be generated. The method also includes introducing a sensor including a shell that contains a ferrofluid in proximity to the magnetic field. The ferrofluid causes distortion of the magnetic field when the ferrofluid is in proximity to the magnetic field. The method also includes receiving, from one or more field measuring coils, a signal representative of a characteristic of the magnetic field measured when the ferrofluid is in proximity to the magnetic field. The method also includes determining one or both of a position and an orientation of the sensor based on the measured characteristic of the magnetic field.

The details of one or more embodiments of the subject matter described herein are set forth in the accompanying drawings and the description below. Other features, objects, and advantages of the subject matter will be apparent from the description and drawings, and from the claims.

DESCRIPTION OF DRAWINGS

Like reference symbols in the various drawings indicate like elements.

DETAILED DESCRIPTION

An Electromagnetic Tracking (EMT) system can be used in medical settings, virtual reality (VR) settings, augmented reality (AR) settings, etc., to track a device. For example, in a surgical setting, the EMT system can be used to track medical equipment, robotic arms, etc., thereby allowing the three-dimensional location and the orientation of the device to be known to a medical professional (e.g., a surgeon) during a medical procedure. Such electromagnetic tracking within the body of a patient can be used for guidance purposes in image-guided procedures, and in some cases may allow for reduced reliance on other imaging modalities, such as fluoroscopy, which can expose the patient to health risk of ionizing radiation.

Figure 1:
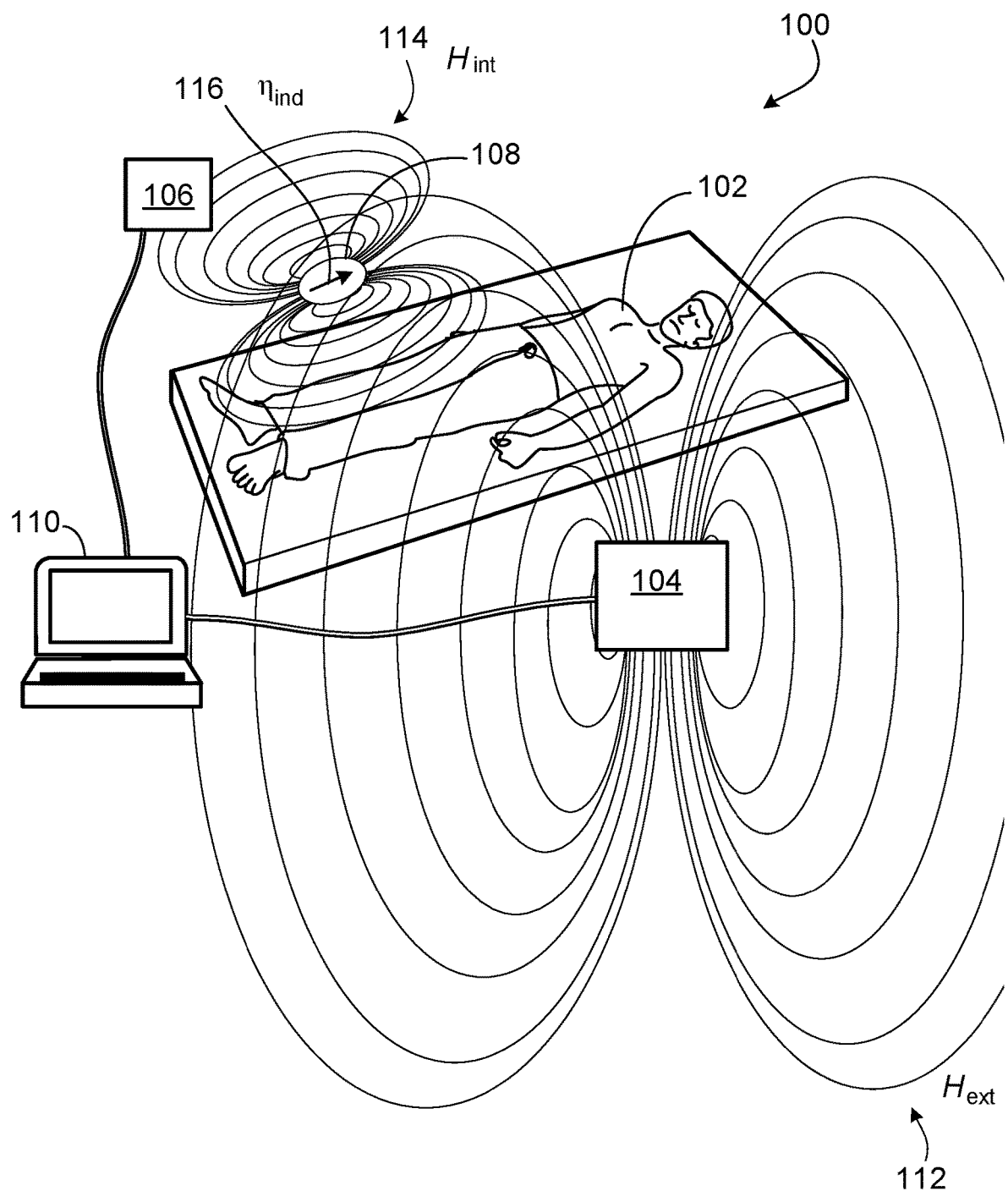
FIG. 1 is a schematic diagram of an Electromagnetic Tracking (EMT) system that includes a field generating coil, a field measuring coil, and a sensor.
Figure 2:
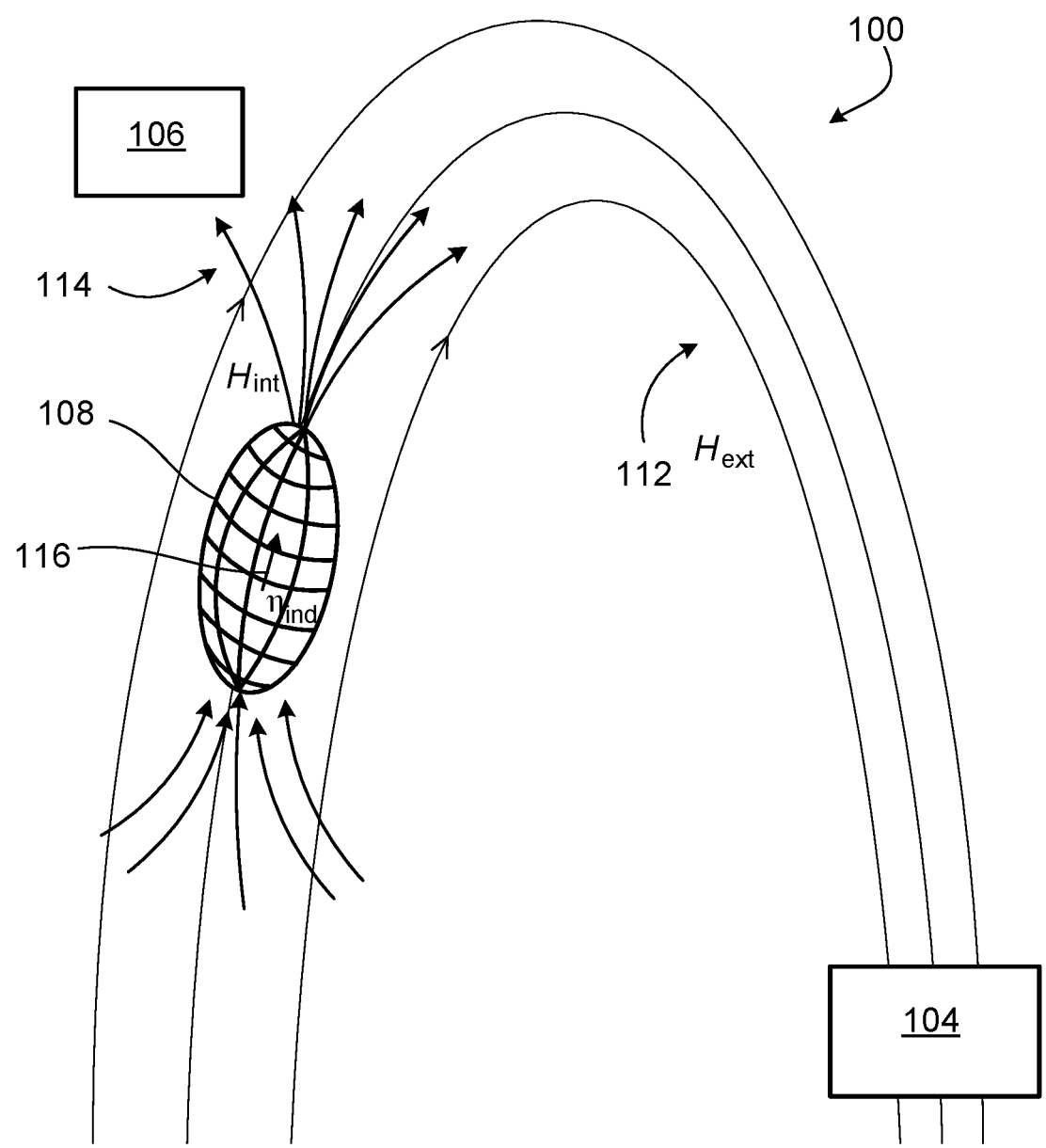
FIG. 2 shows examples of the magnetic fields present in the EMT system.

FIGS. 1 and 2 present an exemplary embodiment of an EMT system 100, which can be used for image-guided medical procedures performed on a patient 102. The system can permit targeting of an anatomical organ, structure, or vessel for visualization, diagnostic, interventional purposes, etc. In general, the system 100 includes one or more field generating coils 104 that are configured to generate a magnetic field 112 (Heat). The system 100 also includes one or more field measuring coils 106 that are configured to measure characteristics of the magnetic field 112. When an object having magnetic properties is introduced to the system 100 (e.g., in proximity to the field generating coils 104 and/or the field measuring coils 106), the generated magnetic field 112 is distorted. The field measuring coils 106 are configured to measure characteristics of such distortions and provide the measurements to a computing device 110. The computing device 110 is configured to determine information related to the object (e.g., one or both of position and orientation information) based on the measurements. The characteristics of the distortions can include characteristics such as field strength, among others. In some implementations, the field strength projected on the field measuring coils 106 (i.e., the one field component of a 3D field vector in the local coil-coordinate system) is measured. In some implementations, full 3D knowledge may be obtained from the measurements of the characteristics of the distorted magnetic field.

For example, the object that is introduced to the system 100 may be a sensor 108 that may employ a wired or wireless architecture (illustrated as wireless). The sensor 108 includes a ferrofluid (304 of FIG. 3) that can have one or more magnetic properties. In particular, the ferrofluid 304 is a fluid that becomes magnetized in the presence of a magnetic field (e.g., the magnetic field 112). Thus, when the sensor 108 is in proximity to the magnetic field 112, the sensor 108 causes distortion of the magnetic field 112. In other words, the sensor 108 interacts with the magnetic field 112 generated by the field generating coils 104 to create a distorted magnetic field 114 ($H_{int}$). An induced moment 116 ($\eta_{ind}$) is also created in the sensor 108. The characteristics of the distorted magnetic field 114 can correspond to the position (e.g., x, y, z coordinates) and orientation (azimuth ($\psi$), altitude ($\theta$), roll ($\varphi$) angles) of the sensor 108. Therefore, the field measuring coils 106 can measure the characteristics of the magnetic field (e.g., the magnetic field 112 when the sensor 108 is not present and/or the distorted magnetic field 114 when the sensor 108 is present), provide a signal representative of the measured characteristics to the computing device 110, and the computing device 110 can determine one or both of the position and the orientation of the sensor 108 based on the measurements. In this way, the sensor 108 may act as a six degree of freedom (6DoF) sensor that is configured to allow for measurement of position and orientation information related to forward/back position, up/down position, left/right position, azimuth, altitude, and roll.

As illustrated in FIG. 1, the field generating coils 104 (e.g., sometimes referred to as field coils) and the field measuring coils 106 (e.g., sometimes referred to as pick-up coils) may be connected to the computing device 110 by a wired connection, although wireless connections are also possible. The location of the field generating coils 104 and the location of the field measuring coils 106 may be known to the computing device 110 (e.g., in terms of x, y, and z coordinates relative to the computing device 110). The field measuring coils 106 may measure one or more characteristics of the magnetic field 112 generated by the field generating coils 104 without the sensor being present, for example, to obtain a baseline magnetic field measurement. A signal representative of the measured characteristics may be provided to the computing device 110.

In some implementations, the field generating coils 104 may be positioned at a surgical drill, at a surgical table (e.g., incorporated into the surgical table), and/or placed somewhere at/near the patient 102. The field measuring coils 106 may be positioned at a location spaced from the field generating coils 104 (e.g., at a location different from the location of the field generating coils 104). In some implementations, the field measuring coils 106 may be positioned at the surgical drill, at the surgical table, and/or placed somewhere at/near the patient 102. In some implementations, the field generating coils 104 or the field measuring coils 106 may be incorporated into a ring that is placed around a leg of the patient 102.

In some implementations, a sensor array may be used to track the location at which the field generating coils 104 are positioned. For example, a sensor array (e.g., a repeater) may be positioned at a location spaced from the field generating coils 104 to track the location of the field generating coils 104 (and, e.g., the surgical drill). In some implementations, such as implementations in which the EMT system 100 is relatively over-determined (e.g., including a relatively large number of field generating coils 104 and field measuring coils 106, such as eight or more of each coil), a solution to the relative positions of the field generating coils 104, the field measuring coils 106, and the sensor array may be numerically determined. In such implementations, the sensor array may also be positioned at the surgical drill such that the field generating coils 104 and the sensor array have a fixed position relative to each other.

The sensor 108 may be introduced in proximity to the magnetic field 112 in a wireless manner (e.g., such that the sensor 108 is not physically connected to the computing device 110). For example, the sensor 108 may be incorporated into a medical device that is to be tracked during a medical procedure. The ferrofluid 302 of the sensor 108 (and, e.g., any other magnetic and/or metallic portions of the sensor 108) causes the magnetic field 112 generated by the field generating coils 104 to be distorted. That is, magnetic properties of the sensor 108 cause the magnetic field 112 near the sensor 108 to be distorted. Such change and/or distortion is illustrated by the distorted magnetic field 114. Characteristics of the distorted magnetic field 114 depend on the position and orientation of the sensor 108. For example, when the sensor 108 is located at a first position, the distorted magnetic field 114 may have a first shape and/or intensity; when the sensor 108 is located at a second position, the distorted magnetic field 114 may have a second shape and/or intensity; when the sensor 108 is located at the second position but has a different orientation, the distorted magnetic field 114 may have a third shape and/or intensity, etc. The field measuring coils 106 are configured to measure one or more characteristics of the distorted magnetic field 114 (e.g., characteristics that correspond to the shape and/or intensity of the magnetic field) and provide a signal representative of the measured characteristics to the computing device 110.

The computing device 110 is configured to determine one or both of the position and the orientation of the sensor 108 based on the received signal representative of the measured characteristics of the distorted magnetic field 114. In some examples, the computing device 110 may determine the position and/or orientation of the sensor 108 relative to the position and/or orientation of the computing device 110, the position and/or orientation of the field generating coils 104, the position and/or orientation of the field measuring coils 106, etc. In some implementations, the computing device 110 may determine the position and/or orientation of the sensor 108 by comparing measured characteristics of the magnetic field 112 (e.g., when the sensor 108 is not present) to measured characteristics of the distorted magnetic field 114 (e.g., when the sensor 108 is present). One or more algorithms or mathematical formulas may be used to determine the position and/or orientation of the sensor 108.

Figure 3:
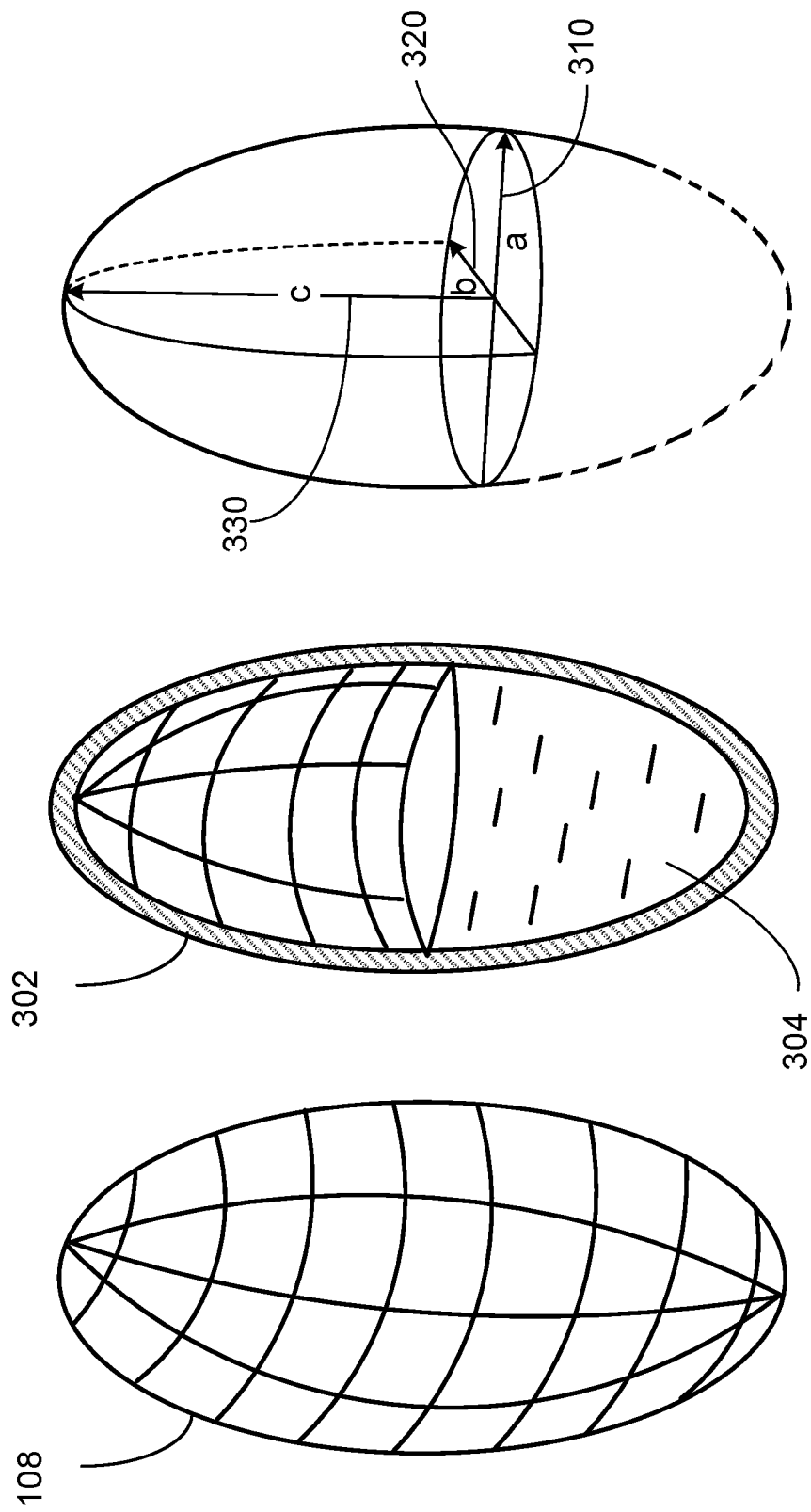
FIG. 3 shows an example of the sensor of the EMT system having an ellipsoid shape.

FIG. 3 shows an example of the sensor 108 of FIGS. 1 and 2. The sensor 108 includes a shell 302 that contains a ferrofluid 304. In the illustrated example, the sensor 108 has an ellipsoid shape that is defined by three axes: an a-axis 310, a b-axis 320, and a c-axis 330. In the illustrated example, the axes are of unequal length. That is, the a-axis 310 has a length that is not equal to a length of the b-axis 320, and the c-axis 330 has a length that is not equal to either the a-axis 310 or the b-axis 320. Such a configuration ensures that 6DoF tracking can be provided by the sensor 108. For example, because the three axes are of unequal length, the exact position and orientation of the sensor 108 can be ascertained unambiguously. If, for example, the b-axis 320 were the same length as the c-axis 330, the azimuth ($\psi$) orientation component may be unmeasurable. In some implementations, the relationship between the dimensions of the sensor 108 may be different than those shown in FIG. 3 (e.g., depending on the particular application).

The ferrofluid 304 may include any material that has magnetic properties that can influence a generated magnetic field. In some implementations, the ferrofluid 304 includes one or both of a liquid and a powder. In some implementations, the ferrofluid 304 includes iron oxide particles such as superparamagnetic iron oxide nanoparticles (SPIONs). The SPIONs may include magnetite ($Fe_3O_4$), maghemite ($\gamma$-$Fe_2O_3$), etc. In some implementations, the SPIONs may have diameters of between about 1 and 100 nanometers.

In some implementations, one or both of the shell 302 and the ferrofluid 304 may be biocompatible and/or biodegradable. For example, the shell 302 and/or the ferrofluid 304 may be made from a material that is not harmful to living tissue. In some implementations, the shell 302 is made from a polymer and/or a wax that is both biocompatible and biodegradable. In this way, the shell 302 may be left in a patient's body to decompose without harming the patient.

In some implementations, the sensor 108 may be configured to be introduced into a patient's body. For example, the sensor 108 may be incorporated into a surgical tool (e.g., a drill, a scalpel, etc.) that is to be used during a medical procedure. In some implementations, the sensor 108 may be incorporated into a surgical implant (e.g., an intramedullary (IM) nail) that is to be inserted into the patient's body. In particular, the sensor 108 may be positioned within an orifice (e.g., a screw hole) of the IM nail such that the position and/or orientation of the orifice can be tracked after the IM nail has been placed inside the patient's body (e.g., after the IM nail has been inserted into a bone of the patient). By tracking the positioned and orientation of the sensor 108, a medical professional can, for example, determine a location on the exterior of the patient's body from which a screw should be inserted in order to align with the screw hole and secure the implant in place against the bone.

In some implementations, the sensor 108 may be configured to be positioned within the patient's body at locations that are difficult to access. For example, the sensor 108 may be positioned at locations that are proximate to delicate anatomy of the patient (e.g., anatomy that, if damaged, could result in harm to the patient), such as in blood vessels (e.g., in the blood stream), in a tumor, etc.

In some implementations, the sensor 108 may be flexible (e.g., structure, housing, etc. may have limited rigidity). By providing a flexible sensor 108, potential damage to the anatomy of the patient during insertion can be minimized or eliminated. In some implementations, the sensor 108 may be introduced into the patient's body in multiple stages. For example, the shell 302 may first be introduced into the patient's body, and the ferrofluid 304 may then be introduced into the patient's body. In this way, the shell 302 can be inserted into an area of the patient's body that is difficult to access (e.g., due to the reduced dimensions of the unfilled shell 302), and the ferrofluid 304 can be injected into the shell 302 thereafter. Similarly, the sensor 108 may be removed from the patient's body in multiple stages. For example, following a medical procedure, the shell 302 may be pierced and the ferrofluid 304 may be removed. In some implementations, the ferrofluid 304 is removed by piercing the shell 302 and introducing a magnetic force (e.g., a permanent magnet) in proximity to the pierced shell 302. The shell 302 may be removed from the patient's body after removal of the ferrofluid 304. In some implementations (e.g., implementations in which the shell 302 is biocompatible and/or biodegradable), the shell 302 may be left in the patient's body.

In some implementations, the properties of the sensor 108 are such that the magnetic properties of the sensor 108 remain unchanged when mechanical stress is applied to the sensor 108. For example, the ferrofluid 204 may maintain its magnetic properties when exposed to mechanical stress. In this way, the sensor 108 can cause distortion of the magnetic field 112 in a defined way and allow the field measuring coils 106 to measure characteristics of the distorted magnetic field 114 that provide an accurate indication of the position and/or the orientation of the sensor 108. Such accurate measurements can be provided even when the sensor 108 is placed under stress as a result of being introduced into the patient's body.

Figure 4A:
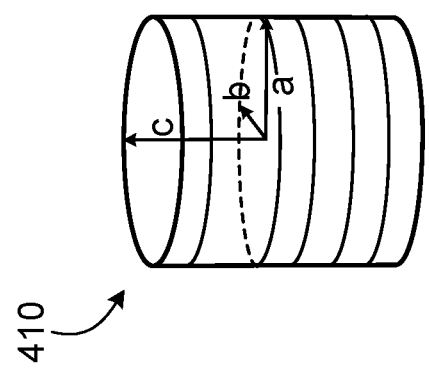
FIGS. 4A-C show other examples of a sensor for an EMT system.
Figure 4B:
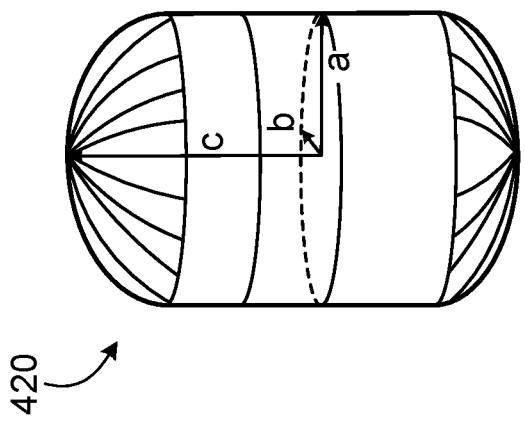
Figure 4C:
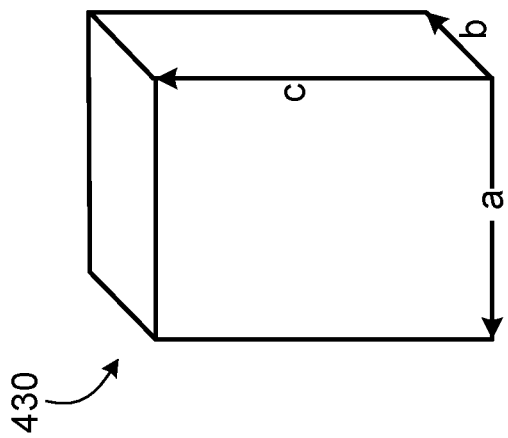

While the sensor 108 has largely been depicted as having an ellipsoid shape, one or more geometries can be employed (that may or may not include an ellipsoid). FIGS. 4A-C show examples of other sensors having various shapes. As shown in FIG. 4A, in some implementations, a sensor 410 for use in the EMT system 100 may have a cylindrical shape. As shown in FIG. 4B, in some implementations, a sensor 420 for use in the EMT system 100 may have a pill shape (e.g., a cylinder with half-spheres on the top and bottom ends). As shown in FIG. 4C, in some implementations, a sensor 430 for use in the EMT system 100 may have a cuboid shape, such as a cube or a rectangular prism. The sensors 410, 420, 430 may have any of a number of dimensions. For example, as described above with respect to FIG. 3, the axes that define each of the sensors 410, 420, 430 (e.g., the a-axis, the b-axis, and the c-axis) may have lengths that are unequal. In some implementations, one or more of the axes may have lengths that are equal to lengths of one or more of the other axes.

The one or more field generating coils 104 (e.g., sometimes referred to as a transmitter) can include a single field generating coil or an array of field generating coils. Similarly, the one or more field measuring coils 106 (e.g., sometimes referred to as a receiver) can include a single field measuring coil or an array of field measuring coils. When an array of coils is used for the one or more field generating coils 106, each coil may be sequentially energized, with each coil creating its own magnetic field and eliciting a different response in the sensor 108. When an array of coils is used for the one or more field measuring coils 108, each coil may be sequentially energized during the time when each field generating coil 106 is energized, with each coil measuring characteristics of the resulting magnetic field (e.g., one or both of the magnetic field 112 and the distorted magnetic field 114).

In some implementations, one or more of the field generating coils 106 may be used for measurement purposes, and one or more of the field measuring coils 108 may be used for field generation purposes. In other words, one or more of the field generating coils 106 may act as field measuring coils 108 and/or one or more of the field measuring coils 108 may act as field generating coils 106. The field generating coils 106 and the field measuring coils 108 may have a configuration and structure that allows for such interchanging of use.

The EMT system 100 described above can be implemented using software included on a computer-readable medium for execution on a computer (e.g., the computing device 110 of FIG. 1). For example, the software may form procedures in one or more computer programs that execute on one or more programmed or programmable computer systems (which may be of various architectures).

Figure 5:
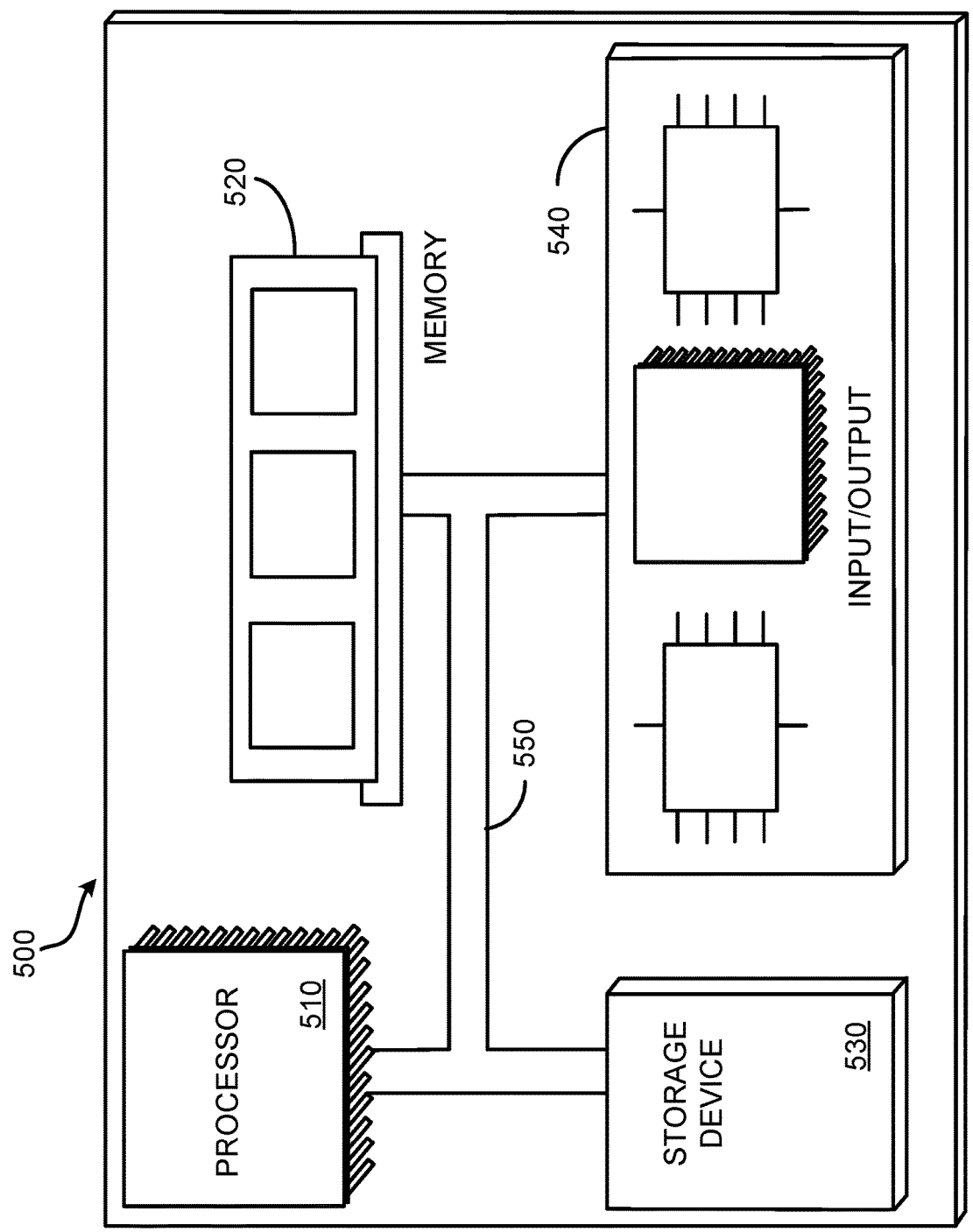
FIG. 5 is a block diagram of an example computer system.

FIG. 5 is a block diagram of an example computer system 500. The computing device 110 of FIG. 1 may be an example of the computer system 500 described here. The system 500 can include a processor 510, a memory 520, a storage device 530, and an input/output device 540. Each of the components 510, 520, 530, and 540 can be interconnected, for example, using a system bus 550. The processor 510 is capable of processing instructions for execution within the system 500. The processor 510 can be a single-threaded processor, a multi-threaded processor, or a quantum computer. The processor 510 is capable of processing instructions stored in the memory 520 or on the storage device 530. The processor 510 may execute operations such as causing the EMT system 100 to determine the position and/or the orientation of the sensor 108.

The memory 520 stores information within the system 500. In some implementations, the memory 520 is a computer-readable medium. The memory 520 can, for example, be a volatile memory unit or a non-volatile memory unit.

The storage device 530 is capable of providing mass storage for the system 500. In some implementations, the storage device 530 is a non-transitory computer-readable medium. The storage device 530 can include, for example, a hard disk device, an optical disk device, a solid-date drive, a flash drive, magnetic tape, or some other large capacity storage device. The storage device 530 may alternatively be a cloud storage device, e.g., a logical storage device including multiple physical storage devices distributed on a network and accessed using a network. In some implementations, the information stored on the memory 520 can also or instead be stored on the storage device 530.

The input/output device 540 provides input/output operations for the system 500. In some implementations, the input/output device 540 includes one or more of network interface devices (e.g., an Ethernet card), a serial communication device (e.g., an RS-232 10 port), and/or a wireless interface device (e.g., a short-range wireless communication device, an 802.11 card, a 3G wireless modem, or a 4G wireless modem). In some implementations, the input/output device 540 includes driver devices configured to receive input data and send output data to other input/output devices, e.g., a keyboard, a printer, and display devices. In some implementations, mobile computing devices, mobile communication devices, and other devices are used.

In some implementations, the system 500 is a microcontroller. A microcontroller is a device that contains multiple elements of a computer system in a single electronics package. For example, the single electronics package could contain the processor 510, the memory 520, the storage device 530, and input/output devices 540.

Although an example computer system has been described in FIG. 5, implementations of the subject matter and the functional operations described above can be implemented in other types of digital electronic circuitry, or in computer software, firmware, or hardware, including the structures disclosed in this specification and their structural equivalents, or in combinations of one or more of them. Implementations of the subject matter described in this specification can be implemented as one or more computer program products, i.e., one or more modules of computer program instructions encoded on a tangible program carrier, for example a computer-readable medium, for execution by, or to control the operation of, a processing system. The computer readable medium can be a machine readable storage device, a machine readable storage substrate, a memory device, a composition of matter effecting a machine readable propagated signal, or a combination of one or more of them.

The term "computer system" may encompass all apparatus, devices, and machines for processing data, including by way of example a programmable processor, a computer, or multiple processors or computers. A processing system can include, in addition to hardware, code that creates an execution environment for the computer program in question, e.g., code that constitutes processor firmware, a protocol stack, a database management system, an operating system, or a combination of one or more of them.

A computer program (also known as a program, software, software application, script, executable logic, or code) can be written in any form of programming language, including compiled or interpreted languages, or declarative or procedural languages, and it can be deployed in any form, including as a standalone program or as a module, component, subroutine, or other unit suitable for use in a computing environment. A computer program does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

Computer readable media suitable for storing computer program instructions and data include all forms of non-volatile or volatile memory, media and memory devices, including by way of example semiconductor memory devices, e.g., EPROM, EEPROM, and flash memory devices; magnetic disks, e.g., internal hard disks or removable disks or magnetic tapes; magneto optical disks; and CD-ROM and DVD-ROM disks. The processor and the memory can be supplemented by, or incorporated in, special purpose logic circuitry. The components of the system can be interconnected by any form or medium of digital data communication, e.g., a communication network. Examples of communication networks include a local area network ("LAN") and a wide area network ("WAN"), e.g., the Internet.

A number of embodiments have been described. Nevertheless, it will be understood that various modifications may be made without departing from the spirit and scope of the subject matter described herein. Other such embodiments are within the scope of the following claims.

What is claimed is:

1. A system comprising:
   one or more field generating coils configured to generate a magnetic field;
   a sensor comprising a shell comprising one or more flexible walls, the shell containing a ferrofluid and configured to be introduced into a patient's body, and wherein the ferrofluid causes distortion of the magnetic field when the sensor is in proximity to the magnetic field and the ferrofluid is configured to be removed from the shell by piercing the shell and introducing a magnetic force in proximity to the shell; and
   one or more magnetic field measuring coils configured to:
      measure a first characteristic of the magnetic field when the sensor containing the ferrofluid is at a first position that is located remote from the magnetic field;
      measure a second characteristic of the magnetic field when the sensor containing the ferrofluid is at a second position that is in proximity to the magnetic field, the sensor being in a first orientation when located at the second position; and
      measure one or more additional characteristics of the magnetic field when the sensor containing the ferrofluid is at one or more positions relative to the magnetic field, each of the one or more positions being different from the second position, the sensor being in a second orientation, different from the first orientation, when located at one of the one or more positions;
   a computing device comprising a processor capable of executing instructions stored on a memory device, that when executed, perform operations comprising:
      receiving one or more signals representative of the first measured characteristic, the second characteristic, and the one or more additional measured characteristics of the magnetic field from the one or more magnetic field measuring coils;
      determining, by the one or more signals, a distortion of the magnetic field, wherein determining the distortion comprises comparing field intensities from the first measured characteristic, the second measured characteristic, and the one or more additional measured characteristics of the magnetic field; and
      determining, based on the distortion of the magnetic field, a position and an orientation of the sensor containing the ferrofluid.

2. The system of claim 1, wherein determining the distortion of the magnetic field comprises comparing shapes and intensities of the magnetic field from the first position, the second position, and the one or more positions.

3. The system of claim 2, wherein the characteristic of the magnetic field measured when the sensor containing the ferrofluid is in the first position comprises a first magnetic shape and a first magnetic intensity, and the characteristic of the magnetic field measured when the sensor containing the ferrofluid is in the second position comprises a second magnetic shape and a second magnetic intensity.

4. The system of claim 3, wherein the one or more additional characteristics of the magnetic field measured when the sensor containing the ferrofluid is at the one or more positions relative to the magnetic field comprises one or more additional magnetic shapes and one or more additional magnetic intensities.

5. The system of claim 2, wherein determining the position and the orientation of the sensor containing the ferrofluid comprises determining the position and the orientation based on the compared shapes and intensities of the magnetic field.

6. The system of claim 1, wherein one or more magnetic properties of the sensor remain unchanged when mechanical stress is applied to the sensor.

7. The system of claim 1, wherein one or both of the shell and the ferrofluid are one or both of biocompatible and biodegradable.

8. The system of claim 1, wherein the ferrofluid comprises one or both of a liquid and a powder.

9. The system of claim 1, wherein the ferrofluid comprises superparamagnetic iron oxide nanoparticles (SPIONs).

10. The system of claim 9, wherein the SPIONs comprise one or both of magnetite ($Fe_3O_4$) and maghemite ($\gamma\text{-}Fe_2O_3$).

11. The system of claim 10, wherein the SPIONs of the ferrofluid have a diameter between 1 and 100 nanometers, inclusively.

12. The system of claim 1, wherein the shell comprises a polymer.

13. The system of claim 1, wherein the ferrofluid in the shell is moveable by a magnetic field.

14. The system of claim 1, wherein the sensor has an ellipsoid shape.

15. The system of claim 14, wherein the ellipsoid is defined by three axes and a length of the ellipsoid along each axis is different.

16. The system of claim 1, wherein the sensor has at least one of (i) a cuboid shape, (ii) a cylindrical shape, or (iii) a pill shape.

17. The system of claim 1, wherein the sensor is wireless.

18. A sensor configured for use in an electromagnetic tracking system, the sensor comprising:
- a shell comprising one or more flexible walls and configured to be introduced into a patient's body; and
- a ferrofluid contained within the shell, wherein the ferrofluid causes measurable distortion of a magnetic field which is comparable to one or more other measured characteristics of one or more magnetic fields by a computing device, wherein the computing device is configured to determine a position and an orientation of the sensor in the magnetic field by determining a distortion of the magnetic field by comparing:
  - a first measured characteristic of the magnetic field when the sensor containing the ferrofluid is at a first position that is located remote from the magnetic field;
  - a second measured characteristic of the magnetic field when the sensor containing the ferrofluid is at a second position that is in proximity to the magnetic field, the sensor being in a first orientation when located at the second position; and
  - one or more additional measured characteristics of the magnetic field when the sensor containing the ferrofluid is at one or more positions relative to the magnetic field, each of the one or more positions being different from the second position, the sensor being in a second orientation, different from the first orientation, when located one of the one or more positions,
- wherein determining the distortion of the magnetic field comprises comparing field intensities from the first measured characteristic, the second measured characteristic, and the one or more additional measured characteristics of the magnetic field, and
- wherein the ferrofluid is configured to be removed from the shell by piercing the shell and introducing a magnetic force in proximity to the shell.

19. A method of tracking a sensor with an electromagnetic tracking system, the method comprising:
- initiating generation of a magnetic field;
- receiving, from one or more magnetic field measuring coils, one or more signals representative of a first measured characteristic, a second characteristic, and one or more additional measured characteristics of the magnetic field, wherein the sensor comprises a shell comprising one or more flexible walls and containing a ferrofluid, wherein the shell is configured to be introduced into a patient's body, wherein the ferrofluid causes distortion of a magnetic field when the ferrofluid is in proximity to the magnetic field and the ferrofluid is configured to be removed from the shell by piercing the shell and introducing a magnetic force in proximity to the shell;
- determining, by the one or more signals and a computing device, a distortion of the magnetic field, wherein determining the distortion comprises comparing field intensities from the first measured characteristic, the second measured characteristic, and the one or more additional measured characteristics of the magnetic field; and
- determining, by the computing device and the distortion of the magnetic field, a position and an orientation of the sensor,
- wherein the first characteristic of the magnetic field is measured when the sensor containing the ferrofluid is at a first position that is located remote from the magnetic field,
- wherein the second characteristic of the magnetic field is measured when the sensor containing the ferrofluid is at a second position that is in proximity to the magnetic field, the sensor being in a first orientation when located at the second position, and
- wherein the one or more additional characteristics of the magnetic field are measured when the sensor containing the ferrofluid is at one or more positions relative to the magnetic field, each of the one or more positions being different from the second position, the sensor being in a second orientation, different from the first orientation, when located at one of the one or more positions.

* * * * *